(12) United States Patent
Friedman

(10) Patent No.: US 7,175,436 B2
(45) Date of Patent: Feb. 13, 2007

(54) OPTICAL COMPOSITE CURE RADIOMETER AND METHOD

(76) Inventor: Joshua Friedman, P.O. Box 2867, Danbury, CT (US) 06813

( * ) Notice: Subject to any disclaimer, the term of this patent is extended or adjusted under 35 U.S.C. 154(b) by 382 days.

(21) Appl. No.: 10/888,638

(22) Filed: Jul. 9, 2004

(65) Prior Publication Data

US 2006/0008762 A1    Jan. 12, 2006

(51) Int. Cl.
*A61C 5/00* (2006.01)
*A61C 3/00* (2006.01)
*G01J 5/02* (2006.01)

(52) U.S. Cl. .................. 433/215; 433/29; 250/340; 250/341.5; 356/432

(58) Field of Classification Search ............. 433/215, 433/29; 356/432; 250/340, 341.5; 362/573
See application file for complete search history.

(56) References Cited

U.S. PATENT DOCUMENTS

| | | | | |
|---|---|---|---|---|
| 3,524,983 A | * | 8/1970 | Voelz ..................... | 250/341.6 |
| 4,874,948 A | * | 10/1989 | Cielo et al. ............... | 250/341.5 |
| 6,089,740 A | * | 7/2000 | Forehand et al. .......... | 362/573 |
| 6,331,111 B1 | * | 12/2001 | Cao ......................... | 433/29 |
| 6,384,099 B1 | * | 5/2002 | Ostler et al. ............... | 522/4 |
| 6,485,301 B1 | * | 11/2002 | Gemunder et al. ......... | 433/29 |
| 7,091,254 B2 | * | 8/2006 | Crivello .................... | 522/1 |

* cited by examiner

*Primary Examiner*—John J Wilson

(57) ABSTRACT

A radiometer and method for providing an indication of the amount of time (exposure duration) needed to cause a light curable dental resin composite material to maximally polymerize in response to the application of light from any light-curing source during the preparation of a dental restoration. It describes a radiometer comprising a sample holder of a size designed to hold a sample equivalent of said dental light curable dental material such that the thickness of the sample of light curable material in the sample holder will correspond to the depth of the composite material in the dental restoration; a solid state light sensor; a microprocessor programmed to respond to the output voltage or change in electrical resistance of the light sensor based upon an algorithm defining a mathematical model representative of the change in light transmission through the light curable dental material as a function of the degree to which said light curable dental material is being polymerized. It includes a time display that is responsive to the output signal generated from the microprocessor for displaying the amount of time (exposure duration) needed to maximally polymerize the light curable dental material in the dental restoration.

12 Claims, 7 Drawing Sheets

Plot of average voltage response to two sequential exposures of light without composite in place.

Monomer Conversion change and light exposure with respect to time.

Change in light transmission during composite curing with respect to time.

Overlay of millivoltage change and composite curing

Correlation of millivoltage change with composite cure at similar points in time during a 40-second exposure

OPTICAL COMPOSITE CURE RADIOMETER AND METHOD

FIELD OF INVENTION

This invention relates to the field of radiometers and more particularly to a dental radiometer for providing the exposure time required to polymerize a light curable composite independent of light source.

BACKGROUND ART

Dentistry has used light curable composite resins for over 20 years with great success for preparing restorations, cementation of restorations, and a number of other dental restorative procedures such that light curing is now a standard procedure in dentistry.

Initial curing lights consisted of halogen devices, first with light sources removed from the point of application and thereafter with light transmitted to the point of application through long fibers. Following that, light curing guns were introduced. These devices typically used halogen light sources with short fused fiber optic light guides close to the lamp to apply high intensity light at the point of application. Along the way, radiometers were introduced into the dental profession for the purpose of measuring light output as a means of assessing the curing light's ability to properly polymerize the dental restorative materials.

Halogen curing lights suffer from a wide variety of mechanisms that cause degradation of intensity. These mechanisms include loss of light output from the halogen lamp, filter degradation, buildup of resin on light guides, degradation of light guides due to sterilization and faulty voltage control circuitry. The radiometer, therefore, has become widely accepted as a means of assessing light output of these devices and indirectly determining whether or not a material or restoration will be properly polymerized.

The popular radiometers in dentistry use either silicon or selenium detector cells with filters that block energy outside of the 400–500 nanometer range. Initially, radiometers were developed specifically for use with halogen light sources with their filters matched fairly closely to the wavelength distribution of the curing lights themselves. In recent years, other types of light sources have been introduced, namely plasma arc or gas pressure lamp devices, using xenon lamps to produce high intensity light in the 400–500 nanometer range. More recently, light emitting diodes (LED's) have been used to produce light specifically peaking at 470, 450 or 420 nanometers that match the absorption characteristics of photoinitiators currently used in dentistry to polymerize these restorative materials. However, when one uses a different light source on the same radiometer designed for halogen usage, erroneous readings result. Accordingly, to properly use a radiometer, the radiometer must be calibrated for use relative to a given light source and no standard of comparison exists to permit comparing the results between radiometers calibrated for different light sources.

The National Institute of Standards and Technology (NIST) presently requires every radiometer to be designed specifically for the light source it's being used with. Moreover, even if one were to use a separate radiometer designed specifically for each of the three types of light sources currently used in dentistry, the problem would still remain as to how long to expose the material under a given set of conditions i.e. depth, shade, and type of material.

Researchers in the dental field typically use a sensitive analytical laboratory tool employing a technique called Fourier Transform Infrared Spectroscopy (FTIR) to determine when a light curable material is maximally polymerized by measuring the ratio of aliphatic carbon-to-carbon double bonds pre- and post-exposure. Such laboratory equipment costs thousands of dollars and is clearly beyond the practical needs of the clinical dentist It would therefore be desirable to have a simple radiometer device that can assess the degree of polymerization and not be affected by which type of light source is used. It would further be desirable for the dentist to be able to determine the exposure time necessary to effect maximal polymerization of the restorative material selected for use in the preparation of a given restoration independent of the light source used to cure the material.

SUMMARY OF INVENTION

The present invention provides the dentist with a simple and effective method and radiometer device for determining the exposure time that provides maximal polymerization of a light curable composite material independent of which light source is used to polymerize the material. The radiometer of the present invention operates by exposing a test sample of light curable material to light regardless of which light source is used and calculates the exposure time necessary to achieve maximal polymerization with that light source. The selected test sample of material is placed in a sample holder in the radiometer which is designed in accordance with the present invention. The exposure time is automatically calculated to achieve maximal polymerization for the test sample of material and will correspond to the time necessary to achieve polymerization of the actual restorative material selected for use in the preparation of a given restoration when the actual restorative material is of identical composition to the test sample and the light source is the same as used to expose the test sample.

DETAILED DESCRIPTION OF INVENTION

Figure 1:
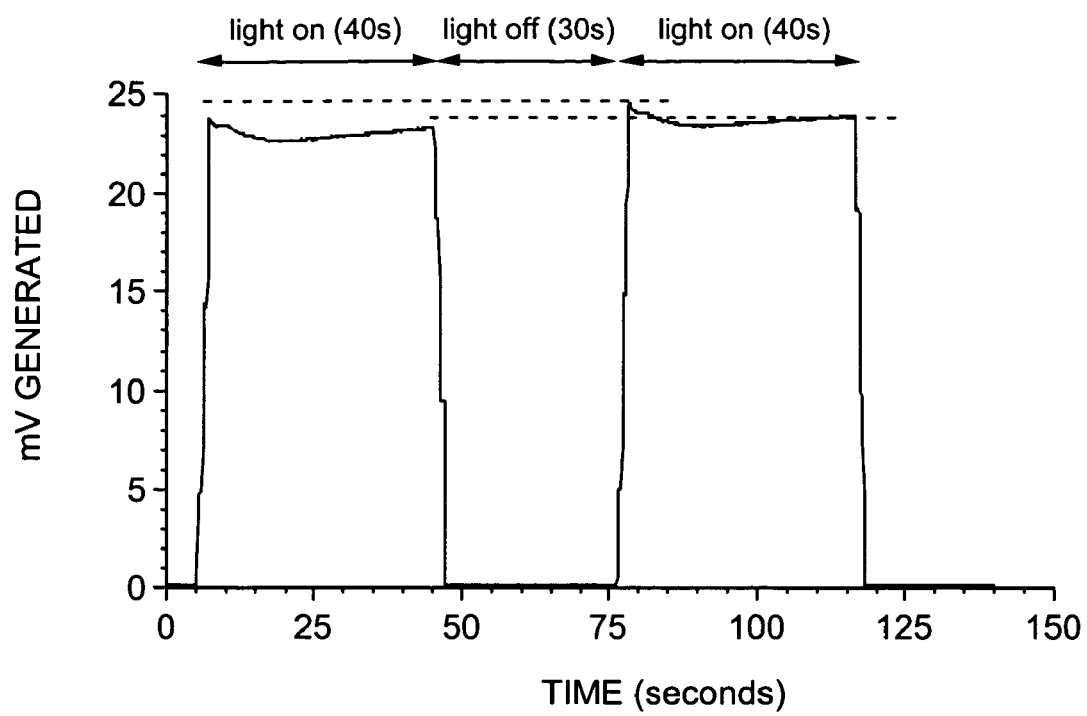
FIG. 1—is a graph of the light detector response (output voltage measured in millivolts) of a conventional radiometer when exposed to light with respect to time over two independent 40-second exposures spaced 30 seconds apart, with no interposing photocurable composite sample between the light tip end and the radiometer detector.

The subject invention results from experimental evidence proving that there Is a direct correlation between the percent composite cure of a light curable resin material and the degree of light transmission through the material as measured by the output of the light detector cell. To substantiate this correlation, the output voltage of a light detector cell in a conventional radiometer was measured based solely upon exposing the detector cell to light. FIG. 1 is a graph showing the relationship between the output of a standard light detector cell with time over two sequential 40 second exposures spaced 30 seconds apart. As can be seen from this graph, whenever the detector cell is subjected to the light source under the same conditions by e.g. turning the light source on and off, a voltage (in millivolts) is generated by the detector cell with the output over each consecutive time period being essentially identical to one another within very dose tolerances. In the tests performed, the differences between the first and second light exposures was only about 0.75 millivolts, and for purposes of the present invention, may be deemed insignificant.

Figure 2:
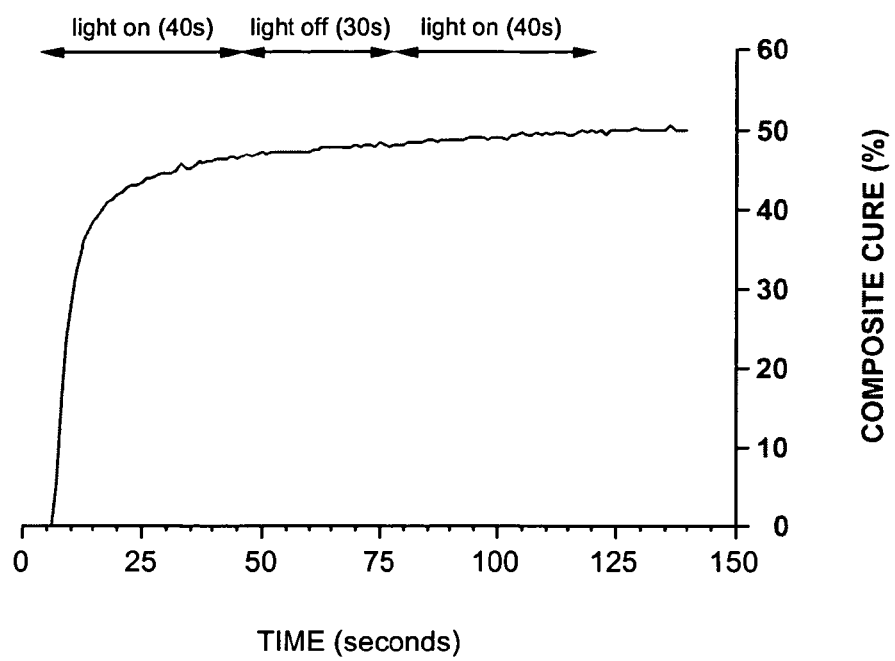
FIG. 2—shows the real-time polymerization of a sample of light curable resin material being exposed to a conventional light-curing source for 40 seconds with respect to time.

FIG. 2 shows the real-time curing profile of a sample of light curable material exposed to a light source (obtained using FTIR spectroscopy) indicating the change in composite cure of the material with respect to time. As noted previously, 2 successive 40-second exposures were given, 30 seconds apart as was the case in FIG. 1 as well. Note the plateau for maximal exposure of this sample of material is reached in approximately 125 seconds, and that no additional curing occurs from the second exposure, but cure increases slowly as a result from the previous exposure (a finding well established in the literature).

Figure 3:
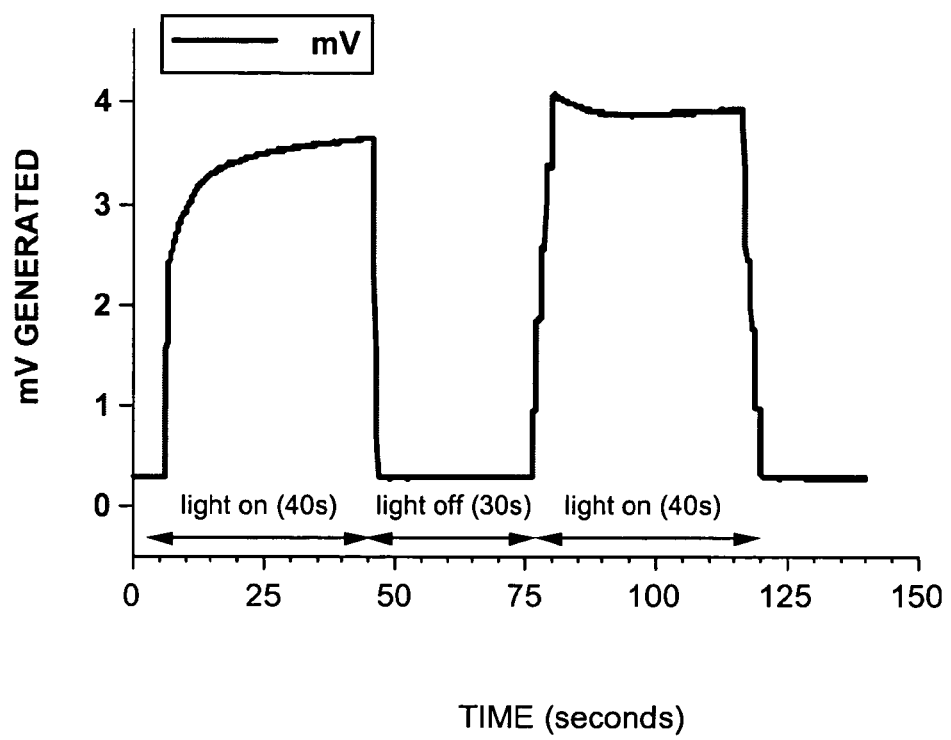
FIG. 3—is a graph of real-time change in radiometer detector response when a 2 mm-thick increment of uncured composite paste is interposed between the light tip and the light detector while giving two sequential 40-second exposures, spaced apart by a 30 second non-exposure time interval FIG. 4—is a graph of FIGS. 2 and 3 superimposed upon one another using the same time scale to demonstrate that the same trend In light detector response while photo-curing composite (FIG. 2) correlates well with changes seen in measuring the real-time polymerization (FIG. 3)
Figure 4:
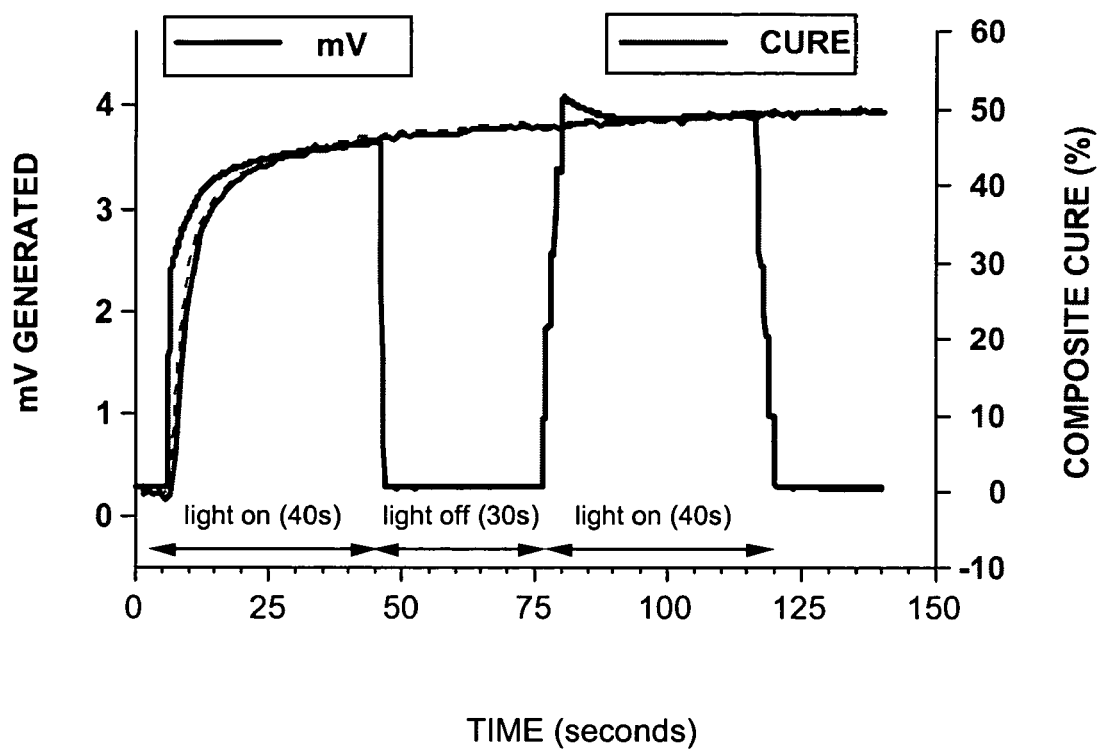

FIG. 3 shows the change in light detector response as measured by millivoltage response when a sample of uncured composite (of similar thickness to that as the specimen used for FIG. 2) as it is exposed to 2 sequential 40 second exposures spaced 30 seconds apart. The same light source was used for both test conditions. Note that during the first exposure, light transmission increases with exposure time resulting in a plateau. Upon second exposure, no obvious trend is seen to relate the second exposure with a change in detector output other than that which would be a slow, continuous increase resulting from the first exposure. Upon overlapping FIG. 2 and FIG. 3 on the same time scale (FIG. 4), it becomes evident that extent of cure of the light curable material and the change in light transmission, noted as an increase in detector millivoltage response, appear to be related and follow one another very closely with respect to time. Although a slight deviation from one wave to the other (0.75 mv) was noted during the first two exposures in FIG. 1, the graph of FIG. 4 shows that light transmission and conversion are essentially identical at the end of the second exposure. Accordingly, this deviation can be ignored.

Figure 5:
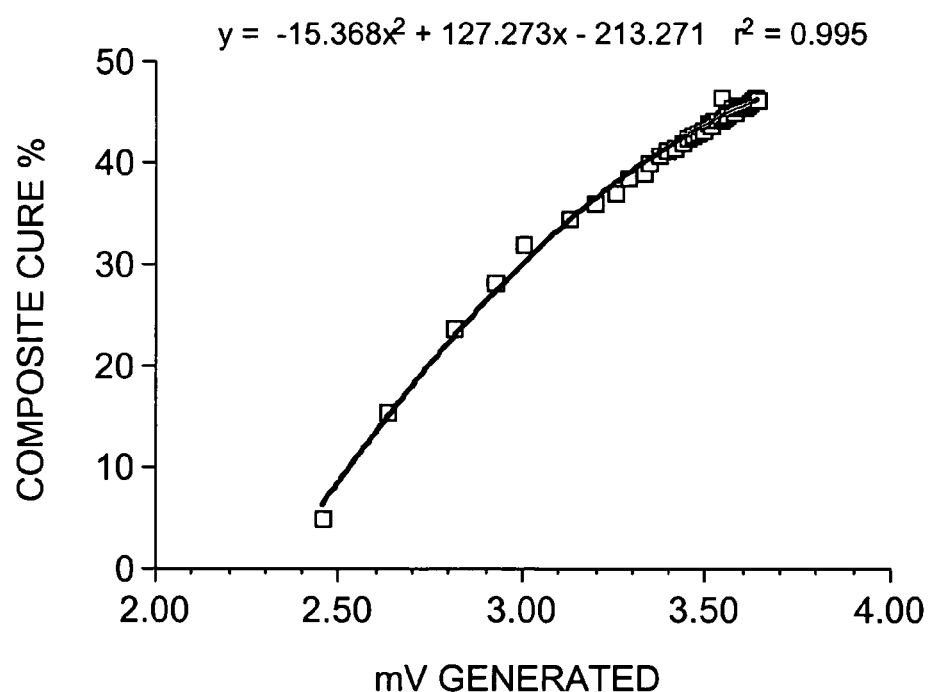
FIG. 5—shows the values of composite cure and light detector response occurring at similar time points as seen in FIG. 4. The data presented are the same as in FIG. 4, but with each "x" marking the correlation of detector response with real-time cure at similar time points (seconds) into giving the 2 sequential 40 second exposures spaced 30 seconds apart.

Eliminating time as a separate axis and correlating composite cure with voltage output at similar time points is shown in FIG. 5, based upon measured data points taken at fixed intervals in time e.g. once per second. As millivoltage generation increases, the percentage of composite cure also increases and they tended to accumulate in the same portion of the graph, which indicates the existence of a point of diminishing return for either parameter. Stated otherwise, the data points tend to accumulate on the right side of the graph corresponding to where composite cure and millivoltage are maximal. This finding indicates that the effect of further light exposure would be insignificant. A curve can be mathematically derived that simulates this relationship based on measured data from which a mathematical model can be predicated with millivoltage generation predicting the extent of composite cure. These results show that an algorithm can be written with an accuracy of up to 99.5%, showing the change of light transmission can be used to accurately predict when the composite cure value will reach a plateau with respect to exposure duration. In this way, the time it takes for any specific light curing composite to approach maximum monomer conversion can be accurately determined. The relationship shown for this specific example in FIG. 5 shows the shape of the algorithm, $Y=-15.368x^2+127.273X-213.217$ having a coefficient of correlation $r^2$ of 0.995, where Y=percent composite cure and X=detector millivoltage output. The coefficient of correlation, $r^2$, is a number between 0 to 1, with 0 indicating absolutely no correlation between factors, and 1 representing complete correlation. Thus, the observed correlation of 0.995 shows a great predictability of millivoltage change being an indicator of the level of composite cure. The value actually indicates that of 100% of the variability seen in the data, the predicted model can explain 99.5%, leaving only 0.5% attributed to unexplained error.

The present relationship uses a second order polynomial to describe the correlation between change in optical density (represented by change in detector millivoltage response) and change in composite cure (extent of polymerization). Thus, a change in light detector output can accurately predict a level of composite cure. Other mathematical algorithms may be applied as well, such as higher degree polynomial, logarithmic, exponential, power, or a combination of these functions as is well known to those skilled in the art.

DESCRIPTION OF OPERATION OF A PREFERRED EMBODIMENT OF THE INVENTION

Figure 6:
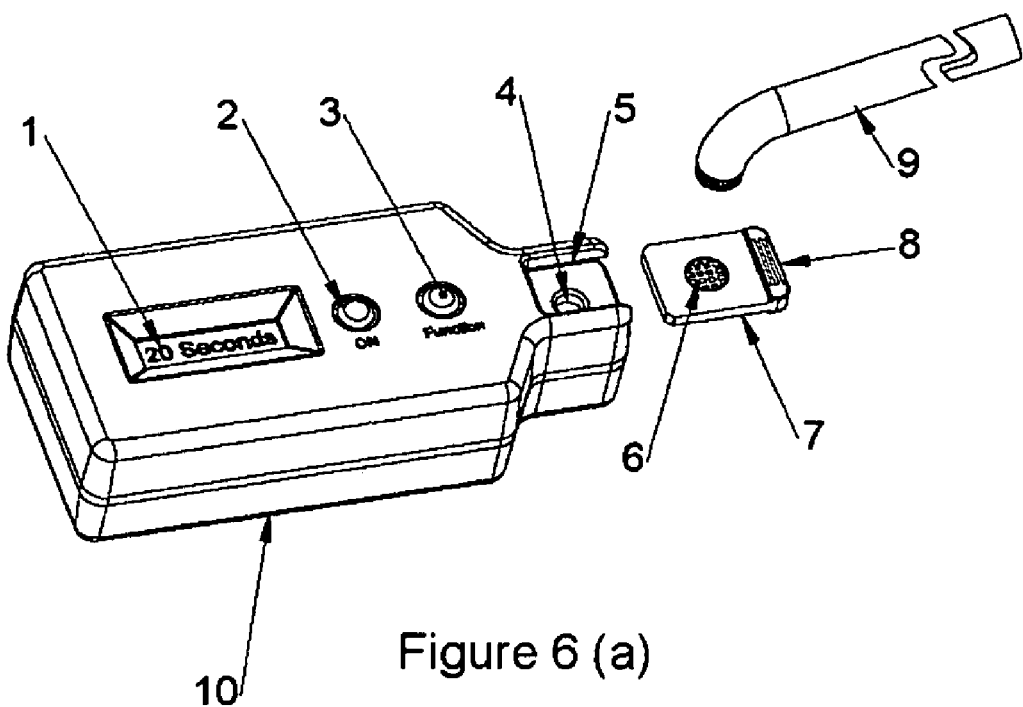
FIG. 6(a)—is a view of the housing assembly of the radiometer of the present invention shown with a sample holder for holding a test sample of light curable material separated from the radiometer adjacent a light guide for a standard light source.
FIG. 6(b)—is another view of the sample holder shown in FIG. 6(a) for holding a test sample of light curable material.
FIG. 6(c)—is yet another view of the sample holder of FIG. 6(b)
Figure 6:
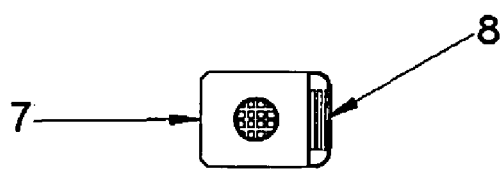
Figure 6:
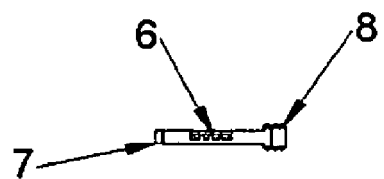
Figure 7:
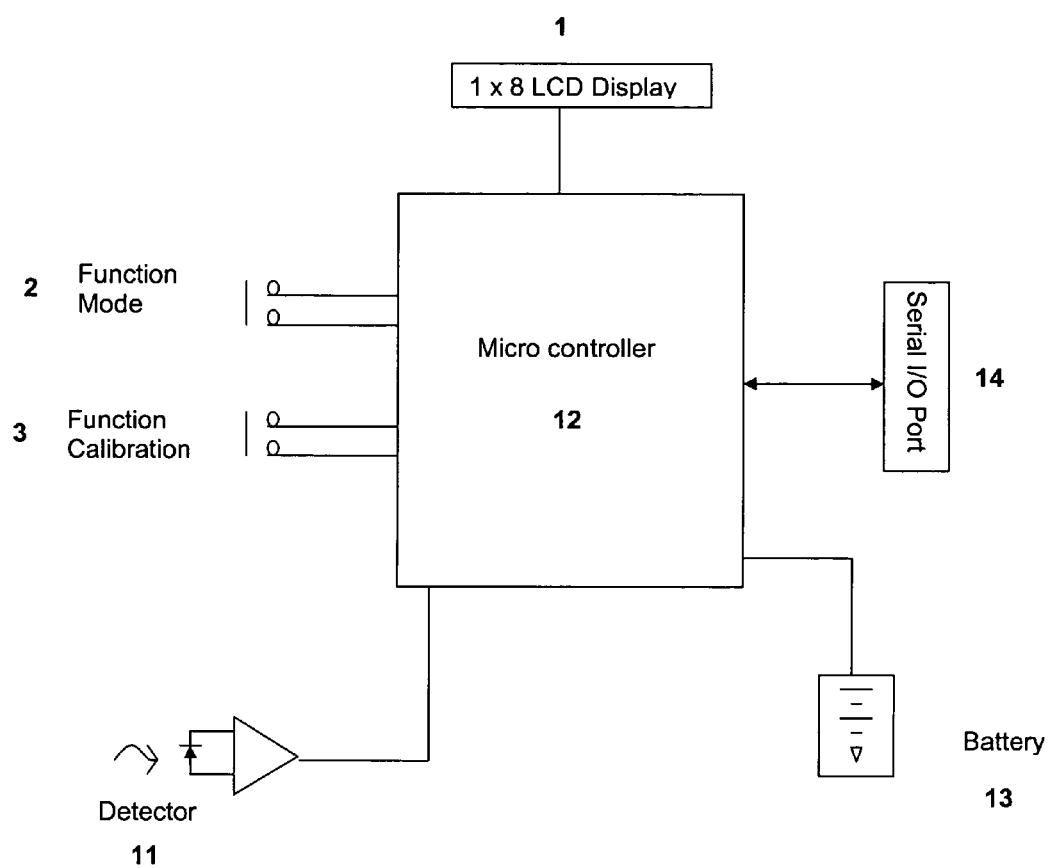
FIG. 7—is a block diagram of the radiometer of the present invention.

The radiometer 10 of the present invention is shown in both FIGS. 6 and 7 with FIG. 7 representing a block diagram of the internal electronic components of the radiometer 10. Accordingly, the radiometer 10 comprises a conventional detector cell 11 which may represent any conventional light sensor such as a silicon or selenium detector cell for providing either an output voltage or a change in electrical resistance in direct response to the degree of light exposure. In addition the radiometer 10 further comprises a microcontroller (microprocessor) 12, battery 13, serial input/output port 14, LCD display 1, an on/off function switch 2, a scroll switch 3, and a mode switch. The function switch 3 permits the radiometer to be scrolled to perform either an "Optical Conversion" function mode, "Power" function mode, "Energy Function" mode, or a "Calibration" function mode. When scrolled to Optical Conversion function mode, the LCD display 1 provides a time display output in seconds that will indicate the shortest exposure time to provide maximal composite cure for a test sample of uncured composite using any type light source as explained hereafter.

Optical Conversion Mode: Any conventional light curing source (not shown) having e.g., a standard light guide 9 may be used to cure a sample of an uncured dental composite 6. The thickness of the sample of uncured composite 6 is adjusted by use of different thickness sample holders 7 with each sample holder 7 having a thickness corresponding to a typical depth of a dental restoration. The sample of composite material 6 is placed in a sample holder 7 of appropriate thickness for a given restoration. It is held by grip detail 8 as shown in FIG. 6c and inserted along a groove or track 5 (FIG. 6a) so that the sample sits directly over the detector window 4 of the light sensor 11, which is shown in FIG. 7. The light guide 9 is placed over the sample in line with the detector window 4 so that light may be shined through the uncured dental composite sample 6. The Function switch 3 is then scrolled to "Optical Conversion" mode of operation. The display 1 will then display time in seconds needed to maximally cure the composite, i.e., will stop when the display shows a time corresponding to the exposure duration needed to achieve the composite cure for the sample composite that represents a time when the sample is cured in accordance with the algorithm used in programming the micro-controller 12. In accordance with the present invention, the micro-controller 12 is programmed using an algorithm such as the one explained earlier. The degree of composite cure measured can be determined to be anywhere between 80% and 99.5% of maximum. It should be understood that, for most composite resin materials, no matter how long the material is exposed to light, the extent of composite cure will plateau at between 45% to 65% of the maximum cure value (100%) for that material, and generally at about 50% as evident from FIG. 2. Thus, for example, using the 2% preferred change as the basis upon which the micro-controller 12 is programmed, when the display times out, the sample has cured to 98% of its maximum achievable value. The micro-controller 12 sampling rate is 0.1 seconds or less to insure accuracy.

Power Mode: When the Function switch 3 is scrolled to "Power Mode" the radiometer 10 will measure the curing light output intensity in watt/cm$^2$ or milliwatt/cm$^2$ and the display 1 for this mode of operation is programmed to update for as long as the push button is held. When the push button is released, the radiometer will continue to measure the curing light output intensity but the display will correspond only to peak measurements.

Energy Mode: When the Function switch (3) is scrolled to "Energy Mode", a momentary push of the Function button will set the energy measured in joules or millijoules to zero (start) and begin to accumulate values once the intensity is above a preset level. The term "energy" is the mathematical product of the power density (measured in W/cm$^2$ or mW/cm$^2$) times the exposure duration (seconds). Thus, as a light exposure continues over time, the accumulated energy delivered to the target also increases and is thus measured by the instrument.

The On button (2) turns the radiometer unit on and it will remain on for two minutes if not used and then will automatically power down to conserve battery life.

Calibration Mode: The radiometer is calibrated at the factory by using a standard lamp and a plastic filter with the same optical transmission characteristics as that of well polymerized dental composite. The user can then compare the exposure time displayed using the calibration filter and the light unit being tested. Comparing the standard reading and the actual value will indicate the offset to which the unit is out of calibration. An auto ranging feature of the micro controller will adjust this offset to zero by holding down the On switch (2) (in the optical conversion mode) and the Function switch (3) simultaneously for two seconds).

LCD Display: This panel will display real-time light intensity (power density), accumulated light energy delivered, or recommended exposure time depending on the mode of operation.

The Light sensor is a solid-state photo detector with 400 to 500 nm sensitivity, but other ranges such as 300–400 nm are possible to measure the intensity of the light coming through the dental composite.

Mode Switch: This switch will allow scrolling through the functions of optical conversion, power and energy.

Function/Calibration Switch: This switch is used to calibrate the radiometer using a standard plastic filter as described previously.

Serial I/O Port: This port is configured as RS232C and will allow two-way communication between the radiometer and a computer or remote display. A "Blue Tooth" or USB Port can also be used. Battery: Two alkaline, lithium or rechargeable batteries power the radiometer. Either button can be pushed to turn the radiometer on, it will remain on for two minutes after the last button is pushed, and then, for battery life conservation the radiometer will go into a "sleep" mode. Low battery indication is evidenced by flashing the display.

Micro controller: The radiometer programs are controlled by a microprocessor. Inputs include measurement of light, reading mode and function switches. Outputs include RS232C or USB communication and display drivers.

The plastic filter is designed to simulate the light transmission characteristics of a well-cured dental composite restoration and can be used for calibration. It may come in four different depths (i.e. 2, 3, 4 & 6 mm) or any depth that is desired. The plastic is selected from a group of plastic materials that have optical transmission characteristics identical to that of a well cured dental restorative material of a given thickness.

What is claimed is:

1. A radiometer for providing an indication of the exposure time needed to cause a light curable dental resin composite material to polymerize in response to the application of light from any type of dental light-curing source during the preparation of a dental restoration, said radiometer comprising:

a sample holder of a size designed to hold a sample equivalent of said dental light curable resin composite material such that the thickness of the sample of light curable material in the sample holder will correspond to the depth of the resin composite material in said dental restoration;

a solid state light sensor located in said radiometer in direct proximity to said sample of light curable material for generating an output in response to the exposure of said sample of light curable material to light from a dental light-curing source;

a microprocessor programmed to respond to the output from said light sensor in accordance with an algorithm defining a mathematical model representative of the change in light transmission through said dental light curable composite material as a function of the extent to which said dental light curable composite material is being polymerized in response to such light and for generating an output signal when the polymerization of the sample has progressed with respect to time to a degree corresponding to a change in light transmission through the sample of less than a defined percent between 0.5% and 20%; and a time display that is responsive to the output signal generated from said microprocessor for displaying duration in time representing the amount of time needed to polymerize the dental light curable material in the dental restoration to its maximal extent.

2. A radiometer as defined in claim 1 wherein said sample holder comprises a plurality of different size sample members, one of which is selected for said radiometer for holding a desired sample of light curable material simulating a corresponding size and thickness of dental composite in the preparation of a dental restoration.

3. A radiometer as defined in claim 2 wherein said algorithm is an equation which mathematically models the characteristic response of said light sensor to the transmission of light through a light curable material as a function of the extent of composite cure of said material when exposed to light from a given light source.

4. A radiometer as defined in claim 3 wherein said mathematical equation defining said algorithm corresponds to a mathematical function selected from the group consisting of a second or higher order degree of polynomial, logarithmic, exponential, power or combination thereof.

5. A radiometer as defined in claim 4 wherein the degree to which a material is polymerized is within 2% of maximum when the sampling rate is 0.1 seconds.

6. An optical conversion radiometer as defined in claim 4 wherein said algorithm is represented by the following mathematical equation: $Y=0.000X^2+0.005X+2.422$;

Where: Y equals the extent of composite cure and X equals detector output voltage generation.

7. A radiometer as defined in claim 4 wherein said radiometer further comprises an adjustable function switch, which permits operation of the radiometer in different modes of operation.

8. A radiometer as defined in claim 7 wherein said function switch comprises a power mode for measuring the curing light output intensity (power density) in watts/cm$^2$ or milliwatts/cm$^2$ and an energy mode in joules or millijoules.

9. A radiometer as defined in claim 7 wherein said function switch comprises a calibration mode of operation for calibrating the actual radiometer reading of display time against a calibrated standard and means to adjust the offset, if any, to zero.

10. A method for providing a time indication of the amount of time (exposure duration) needed to cause a dental light curable resin composite material to polymerize to maximal extent in response to the application of light from any light-curing source during the preparation of a dental restoration, comprising the steps of:

placing a sample of said dental light curable resin composite material into a radiometer comprising a sample holder designed to hold one of a plurality of different given sizes of said sample of dental light curable material, a solid state light sensor located in said radiometer in proximity to the sample in said sample holder for generating an output voltage or change in electrical resistance in direct response to the exposure of said sample of light curable material to light from a standard light source, a microcomputer programmed to generate an output signal when the sample material is maximally polymerized in response to light from the light source and a time display for displaying the time period starting from the exposure of said sample (exposure duration) to light and ending upon the generation of said output signal;

programming said microcomputer to generate said output signal when the polymerization of the sample has progressed with respect to time to a degree corresponding to a change in light transmission through the sample of less than a defined percent equal to between 0.5% and 20%, based upon the use of an algorithm defining a mathematical model representative of the change in light transmission through said dental light curable composite material as a function of the degree to which said dental light curable composite material is being polymerized in response to such light;

placing the radiometer sample holder containing said sample into close proximity to said standard light source for exposing said sample to the output of a dental light-curing source; and actuating the time display in synchronism with the exposure of said sample of material to light from said light source whereby the time displayed will represent the amount of time (exposure duration) needed to maximally polymerize the dental light curable material in the dental restoration.

11. A method as defined in claim 10 wherein the size of sample selected for placement in said sample holder simulates the size and thickness of dental composite to be used in the preparation of the dental restoration.

12. A method as defined in claim 11 wherein the degree to which a material is polymerized is within 2% of maximum value when the sampling rate is 0.1 seconds.

* * * * *